US010130543B2

United States Patent
Huldin

(10) Patent No.: US 10,130,543 B2
(45) Date of Patent: *Nov. 20, 2018

(54) POSITION-RETAINING DEVICE

(71) Applicant: IZI MEDICAL PRODUCTS, LLC, Owings Mills, MD (US)

(72) Inventor: Nelson L. Huldin, Owings Mills, MD (US)

(73) Assignee: IZI Medical Products, LLC, Owings Mills, MD (US)

( * ) Notice: Subject to any disclaimer, the term of this patent is extended or adjusted under 35 U.S.C. 154(b) by 456 days.

This patent is subject to a terminal disclaimer.

(21) Appl. No.: 15/067,401

(22) Filed: Mar. 11, 2016

(65) Prior Publication Data

US 2017/0258660 A1 Sep. 14, 2017

(51) Int. Cl.
*A61F 5/05* (2006.01)
*A61G 13/12* (2006.01)
(Continued)

(52) U.S. Cl.
CPC ............ *A61G 13/1275* (2013.01); *A61F 5/37* (2013.01); *A61G 7/065* (2013.01); *A61G 13/127* (2013.01);
(Continued)

(58) Field of Classification Search
CPC .. A61F 5/058; A61F 5/05808; A61F 5/05816; A61F 5/05825; A61F 5/05833;
(Continued)

(56) References Cited

U.S. PATENT DOCUMENTS

| 4,388,358 A | 6/1983 | Davis et al. |
| 4,828,325 A | 5/1989 | Brooks |

(Continued)

FOREIGN PATENT DOCUMENTS

| WO | 2006/130818 A2 | 12/2006 |
| WO | 2006130818 A2 | 12/2006 |

OTHER PUBLICATIONS

International Search Report and Written Opinion of the International Searching Authority for PCT/IB2017/051418 dated Jun. 7, 2017.

(Continued)

*Primary Examiner* — Tarla Patel
(74) *Attorney, Agent, or Firm* — Ajay A. Jagtiani

(57) ABSTRACT

In an initial configuration a device comprises a casing containing: a plurality of beads, a rupturable first container containing one or more isocyanates and a rupturable second container containing one or more polyols, wherein in the final configuration the casing is substantially filled by a polyurethane in which the plurality of beads are embedded. In an intermediate configuration the device is transformed from the initial configuration to a final configuration by rupturing the first container and rupturing the second container so that the one or more isocyanates react with the one or more polyols in a reaction that forms the polyurethane. As the polyurethane is formed during the reaction the polyurethane surrounds the plurality of beads. The device may be molded as the polyurethane is formed in the casing.

25 Claims, 9 Drawing Sheets

(51) Int. Cl.
*A61F 5/37* (2006.01)
*A61G 7/065* (2006.01)
*A61N 5/10* (2006.01)

(52) U.S. Cl.
CPC .. *A61G 2210/50* (2013.01); *A61N 2005/1097* (2013.01)

(58) Field of Classification Search
CPC .... A61F 5/05841; A61F 5/0585; A61F 5/019; A61F 5/05858; A61F 5/37; A61F 5/05866; A61F 5/05875; A61L 15/14; A61L 15/125
USPC .......................................................... 602/8
See application file for complete search history.

(56) References Cited

U.S. PATENT DOCUMENTS

| | | | |
|---|---|---|---|
| 5,699,902 | A | 12/1997 | Sperry et al. |
| 5,899,325 | A | 5/1999 | Bertram et al. |
| 7,204,817 | B1 | 4/2007 | Toronto et al. |
| 2017/0258660 | A1* | 9/2017 | Huldin ............... A61G 13/1275 |

OTHER PUBLICATIONS

Office Action received in U.S. Appl. No. 15/168,731 dated Apr. 16, 2018.
Search Report and Written Opinion received in PCT Application No. PCT/IB2017/053214 dated Nov. 14, 2017.

* cited by examiner

US 10,130,543 B2

POSITION-RETAINING DEVICE

BACKGROUND

Field of the Invention

The present invention relates to a moldable position-retaining device.

Related Art

Various outfits and equipment have been used in the fields of medical treatment and patient care and welfare for stabilizing and supporting human bodies on beds, chairs, inspection and examination devices and the like. These outfits and equipment have various deficiencies.

SUMMARY

According to a first broad aspect the present invention provides a device comprising a casing and having: an initial configuration, an intermediate configuration, and a final configuration, wherein in the initial configuration the casing contains: a plurality of beads, a rupturable first container containing one or more isocyanates and a rupturable second container containing one or more polyols, wherein in the final configuration the casing is substantially filled by a polyurethane in which the plurality of beads are embedded, wherein in the intermediate configuration the device is transformed from the initial configuration to the final configuration by rupturing the first container and rupturing the second container so that the one or more isocyanates react with the one or more polyols in a reaction that forms the polyurethane, and wherein as the polyurethane is formed during the reaction the polyurethane surrounds the plurality of beads.

According to a second broad aspect, the present invention provides method comprising: transforming a position-retaining device from an initial configuration to an intermediate configuration, and transforming the position-retaining device from the intermediate configuration to a final configuration, wherein the in the initial configuration, the position-retaining device comprises a casing containing: a plurality of beads, a rupturable first container containing one or more isocyanates and a rupturable second container containing one or more polyols, wherein transforming the position-retaining device from the initial configuration to an intermediate configuration comprises rupturing the first container and rupturing the second container through the casing so that the one or more isocyanates react with one or more polyols in a reaction that forms a polyurethane that surrounds a plurality of beads and substantially fills the casing, wherein transforming the position-retaining device from the intermediate configuration to the final configuration comprises molding the casing around at least a portion of a body part so that the position-retaining device conforms to the at least a portion of the body part while the polyurethane is being formed inside the casing, and wherein after the reaction is finished, the plurality of beads are embedded in the polyurethane so that the position-retaining device permanently conforms to the at least a portion of the body part.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Definitions

Figure 1:
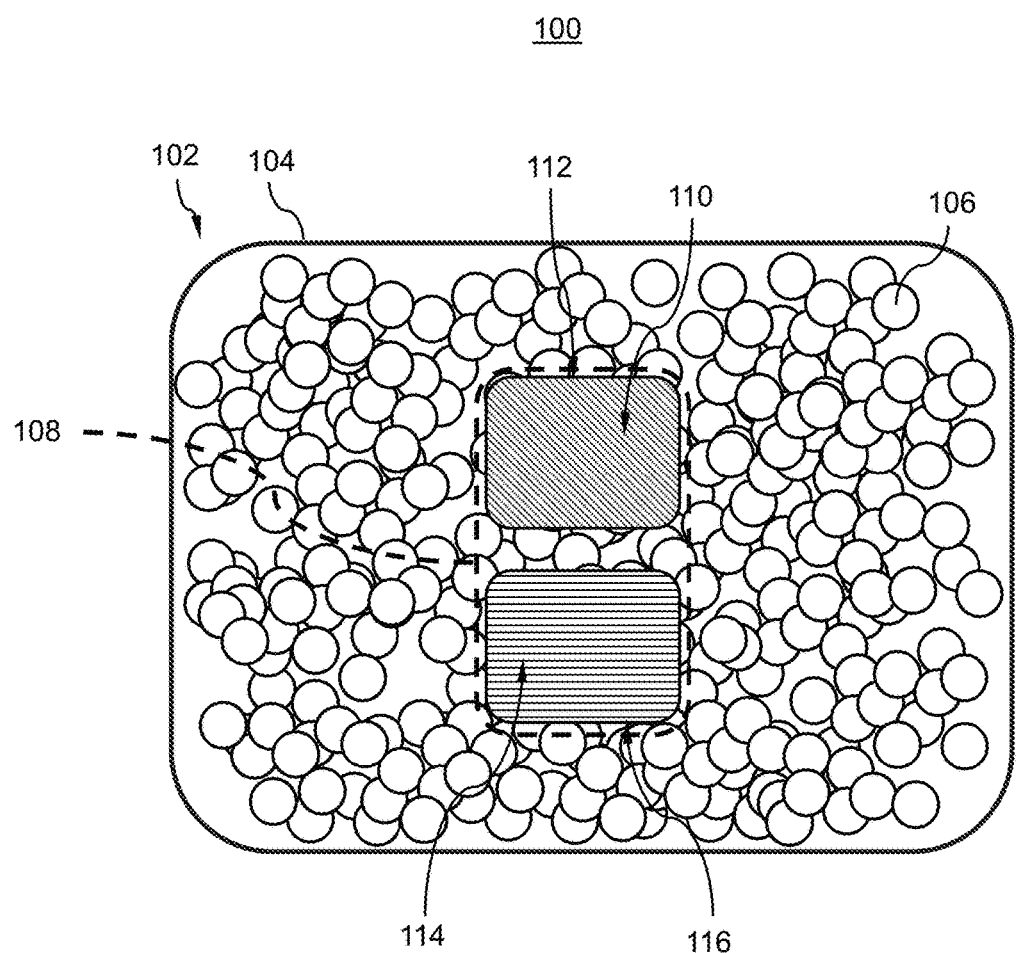
FIG. 1 is a schematic diagram illustrating a stabilizing cushion in an initial configuration, according to one embodiment of the present invention.

Where the definition of terms departs from the commonly used meaning of the term, applicant intends to utilize the definitions provided below, unless specifically indicated.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present invention, the term "comprising", the term "having", the term "including," and variations of these words are intended to be open-ended and mean that there may be additional elements other than the listed elements.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, devices, etc., shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "bead" and the term "beads" refer to any particle that can be embedded in polyurethane. For example, a bead of the present invention may be made of any solid material such as plastic, metal, wood, etc. In one embodiment of the present invention, the beads of the present invention may be plastic beads such as polystyrene beads. The beads of the present invention may be any size that is convenient and any shape that is convenient. The beads may be solid, hollow, porous, comprised of a closed-cell foam, such as a closed-cell extruded polystyrene foam such as Styrofoam®, an expanded plastic such as expanded polystyrene (EPS), etc. The beads may all be the same size or the beads may be a variety of sizes.

For purposes of the present invention, the term "oleophobic vent" refers to a vent made from an oleophobic material, i.e., an oil-fearing material, that allows the free flow of gases but prevents the flow of low surface tension fluids and water through the vent. In one embodiment of the present invention, an oleophobic vent may be a piece of a porous oleophobic membrane, i.e., an oleophobic membrane having pores therein, that resists wet-out from low surface tension fluids, such as oil which has a surface tension of 30 dynes/cm. An example of a porous oleophobic membrane is microporous expanded polytetrafluoroethylene (ePTFE) membrane such as the ePTFE membrane marketed under the name GORE™ Membrane Vents by W. L. Gore & Associates.

For purposes of the present invention, the term "room temperature" refers to a temperature of from about 20° C. to about 25° C.

For purposes of the present invention, the term "rupturable container" refers to a flexible container, such as a sealed pouch, that may be ruptured by hand when the container is filled with a liquid. A rupturable container may including a portion that has been weakened, such as by thinning the material of the container in a region or along a line or pattern. In one embodiment of the present invention, a rupturable container may be a sealed pouch made of aluminum foil, a plastic, etc. that is sufficiently thin that the sealed pouch is rupturable by applying pressure to the sealed pouch through a casing containing the sealed pouch when the sealed pouch is filled with a liquid.

Description

In one embodiment, the present invention provides a moldable position-retaining device which can be made to conform to the configuration of a person's body or body part to provide an anatomically high-accuracy position-retaining device for patient positioning, immobilization, and repositioning during applications requiring a high degree of accuracy in patient positioning.

A position-retaining device of the present invention may be interchangeably described as a stabilizing pillow, cushion, cast, or other terms as would be known in the art. A position-retaining device may also be part of a larger article such as a headrest, an armrest, a chair, a bed, a couch, etc. A position retaining-device of the present invention can be used, among other purposes, to retain the person's body or body part in a required position or attitude with the pressure from the body or body part being distributed such as uniformly and effectively on the position-retaining device. The device, in certain embodiments, is particularly well-suited for patient positioning during radiotherapy or other procedures in which high accuracy and consistent repeatability in positioning are important.

Various types of outfits and equipment have been used in the fields of medical treatment and patient care and welfare for stabilizing and supporting human bodies on beds, chairs, inspection and examination devices and the like. With regard to the securing mechanism by which such various outfits and equipment rigidify in conformation with patient body part, the two primary mechanisms are based on moisture-based activation and heat-based application. In the moisture based approach, a predetermined amount of granulated materials coated with a moisture curable resin is enclosed in a water-permeable container having smaller openings than the size of the granulated materials. The water-permeable material is tightly sealed within a moisture-impermeable container such as an air-tight aluminum foil to prevent moisture from reaching the cushions. To use the cushion, a therapist will remove the packaging and apply water to the fabric of the cushion. The cushion is then placed and shaped under the patient's head or other body part. The inner resin reacts with the water and hardens in about 10 minutes, creating a solid formed support and stabilizing the patient.

A disadvantage of water-activation methods includes scenarios wherein excess water may pose a high risk of adversely affecting the medical instruments if excess water is present during irradiation by radioactive rays of the spot where many precise instruments are to be placed. Furthermore, in some cases, using moisture-activated securing mechanism produces an unpleasant scent associated with activation of the product and, furthermore, it feels sticky to touch. The impracticality of heating the securing process requires an oven, or a hot water bath which may not always be available.

Heat-based approaches using thermoplastics for patient positioning has been described. These position-retaining devices are similarly constructed as their moisture-activated counter-parts but with a different method of becoming secure. These devices generally comprise an inner component of small beads surrounded by a layer of thermoplastic material, such as polycaprolactone, that softens and becomes moldable at high temperatures (target temperature depending on the thermoplastic compound). The thermoplastic layer typically has a soft fabric material surrounding it, for patient comfort. Such a device much first be placed in an oven, or in a hot water bath to heat it to desired temperature at which the device becomes moldable by hand and remains moldable for short period of time. The device remains moldable for a period of time typically in range of 5 to 8 minutes as it cools to room temperature. The position-retaining device hardens to create a firm support cushion, conforming to and stabilizing the patient.

Embodiments of the present invention address the above shortcomings of current position-retaining patient immobility devices by providing a securing mechanism that does not require application of water or heat.

In one embodiment, the present invention provides a moldable stabilizing cushion includes a casing containing beads, such as polystyrene beads, that constitute a deformable inner body of the moldable stabilizing cushion. To bind the beads together and fix the position of the beads in place after the moldable stabilizing cushion has been molded to a desired shape, in an initial configuration, the moldable stabilizing casing contains a two-part binding agent in addition to the beads. The two-part binding agent consists of one rupturable container containing one or more isocyanates and a second rupturable container containing one or more polyols. When the two rupturable containers are ruptured, such as by rupturing the rupturable containers by hand through the casing, the one or more isocyanates and the one or more polyols are released and mix to form a polyurethane that expands to fill or substantially fill the casing and surround the beads. While the polyurethane is being formed and before the polyurethane hardens, the moldable stabilizing cushion is in an intermediate configuration that allows the moldable stabilizing cushion to be molded into a desired shape. After period of time, the polyurethane hardens and the beads are fixed in place so that the moldable stabilizing cushion achieves a final configuration.

In one embodiment of the present invention, while the moldable stabilizing cushion is an intermediate configuration, the moldable stabilizing cushion may be molded around a body part or a portion of a body part so that in the final configuration the moldable stabilizing cushion conforms to the shape of the body part or the portion of the body part and may be used to support the body part or the portion of the body part.

In one embodiment of the present invention, the transformation of the moldable stabilizing cushion from the initial configuration to the intermediate configuration may be achieved by application of pressure upon outer walls of one or more rupturable containers contained in the casing to thereby cause the reagents in the one or more rupturable containers to be released into the space in between and around the beads.

A two-part polyurethane that may be used in various embodiments of the present invention is formed from the reaction of a monomeric or polymeric isocyanate with a polyol. Isocyanates suitable for the purposes of the present invention include one or more isocyanate (NCO) functional groups, typically at least two NCO functional groups. Suitable isocyanates include, but are not limited to, conventional aliphatic, cycloaliphatic, aryl and aromatic isocyanates. Some more specific examples include diphenylmethane diisocyanates (MDIs), polymeric diphenylmethane diisocyanates (PMDIs), and combinations thereof. Polymeric diphenylmethane diisocyanates may be also referred to as polymethylene polyphenylene polyisocyanates. Examples of other suitable isocyanates include, but are not limited to, toluene diisocyanates (TDIs), hexamethylene diisocyanates (HDIs), isophorone diisocyanates (IPDIs), naphthalene diisocyanates (NDIs), and combinations thereof.

Suitable polyols for the purposes of the present invention includes one or more hydroxyl (ROH) functional groups, or more specifically at least two hydroxyl functional groups. A polyol can be any type of polyol. Some examples of suitable polyols include, but are not limited to, ethylene glycol, diethylene glycol, propylene glycol, dipropylene glycol, butanediol, glycerol, trimethylolpropane, triethanolamine, pentaerythritol, sorbitol, and combinations thereof.

FIG. 1 illustrates an initial configuration 100 for position-retaining device 102 according to one embodiment of the present. Position-retaining device 102 includes a casing 104 containing beads 106 and a two-part urethane system 108 consisting of an isocyanate component 110 contained within a rupturable container 112 and a polyol component 114 contained in a rupturable container 116. Isocyanate component 110 may be a single isocyanate or may be a mixture of two or more isocyanates. Polyol component 114 may be a single polyol or may be a mixture of two or more polyols. In this configuration two-part urethane system 108 is inactive, beads are free to move in casing 104 and position-retaining device 102 may be stored until it is ready for use.

In one embodiment the beads may puffed or non-puffed polystyrene bead having a density form 1 to 5 lb/ft$^3$ per cubic foot (16.02 to 80.09 kg/m$^3$).

Although for simplicity of illustration, the rupturable containers are shown in FIG. 1 as being near the top of the moldable position-retaining device and in the center of the position-retaining device. However, in other embodiments of the present invention, the rupturable containers may be located elsewhere within the casing. The two rupturable containers may be located closely together, or even adjacent, as shown, or may be located a distance away from each other in the casing. In one embodiment of the present invention, the rupturable containers may be connected to each other. In one embodiment of the present invention, the rupturable containers may be connected to a prescribed location within the casing, such as at one end of the casing, so that the two rupturable containers may be easily located. In one embodiment of the present invention, there may be two or more rupturable containers for the isocyanate component and two or more rupturable containers for the polyol component. In one embodiment of the present invention, two or more rupturable containers may each contain a different isocyanate. In one embodiment of the present invention, two or more rupturable containers may contain different polyols.

Figure 2:
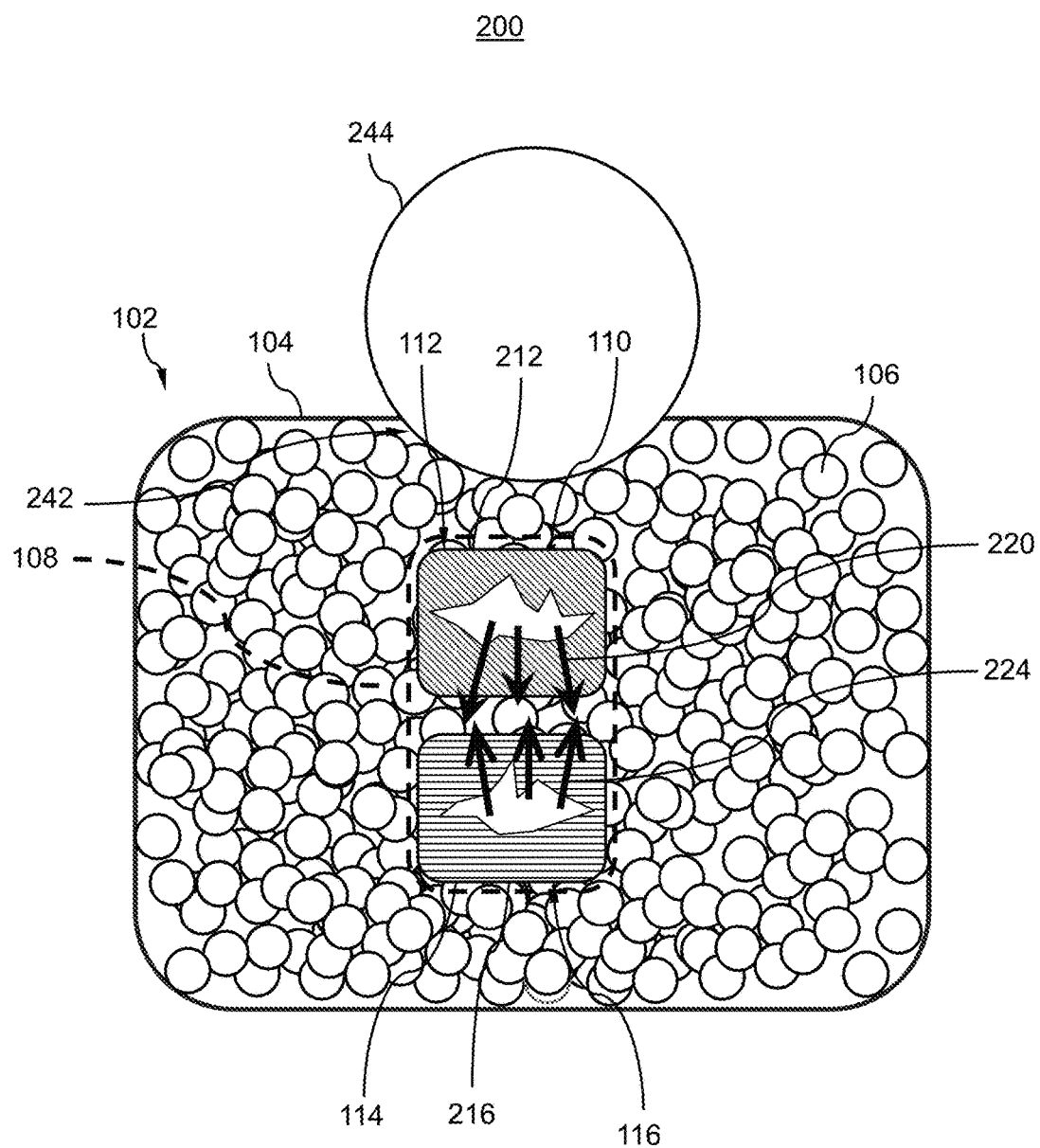
FIG. 2 is a schematic diagram illustrating a stabilizing cushion in an intermediate configuration, according to one embodiment of the present invention.

FIG. 2 shows position-retaining device 102 in an intermediate configuration 200 when two-part urethane system 108 is activated by rupturing rupturable container 112, as shown by rupture 212, and by rupturing rupturable container 116, as shown by rupture 216. Upon rupturing, isocyanate component 110 flows from rupturable container 112, as indicated by arrows 220, and mixes with polyol component 114 flowing from rupturable container 116, as indicated by arrows 224. As isocyanate component 110 and polyol component 114 mix together and react to form a polyurethane, the polyurethane so formed flows around and between beads 106 and fills or substantially fills casing 104. As the polyurethane is being formed, position-retaining device 102 is in the process of being molded by hand around a portion 242 of a body part 244.

The position-retaining device remains deformable for a period of approximately 5 to 10 minutes while in the intermediate condition. During this period of time, the stabilizing may be molded by hand to conform and/or surround a body part or a portion of a body part. Example of body parts and portions of body parts to which the position-retaining device may be conformed or support including an individual's arm, leg, hand, foot, finger or fingers, toe or toes, thigh, calf, ankle, wrist, elbow, knee, head, jaw, back, spine, torso, hip, chest, etc.

The rupturable containers may be ruptured in a variety of ways including by applying pressure to the casing in a single direction to press the casing against a solid surface, such as a table, or by squeezing the casing. The rupturable containers may also be ruptured by using a device to apply pressure in a single direction to the casing against a solid surface, such as a table, or to squeeze the casing.

Figure 3:
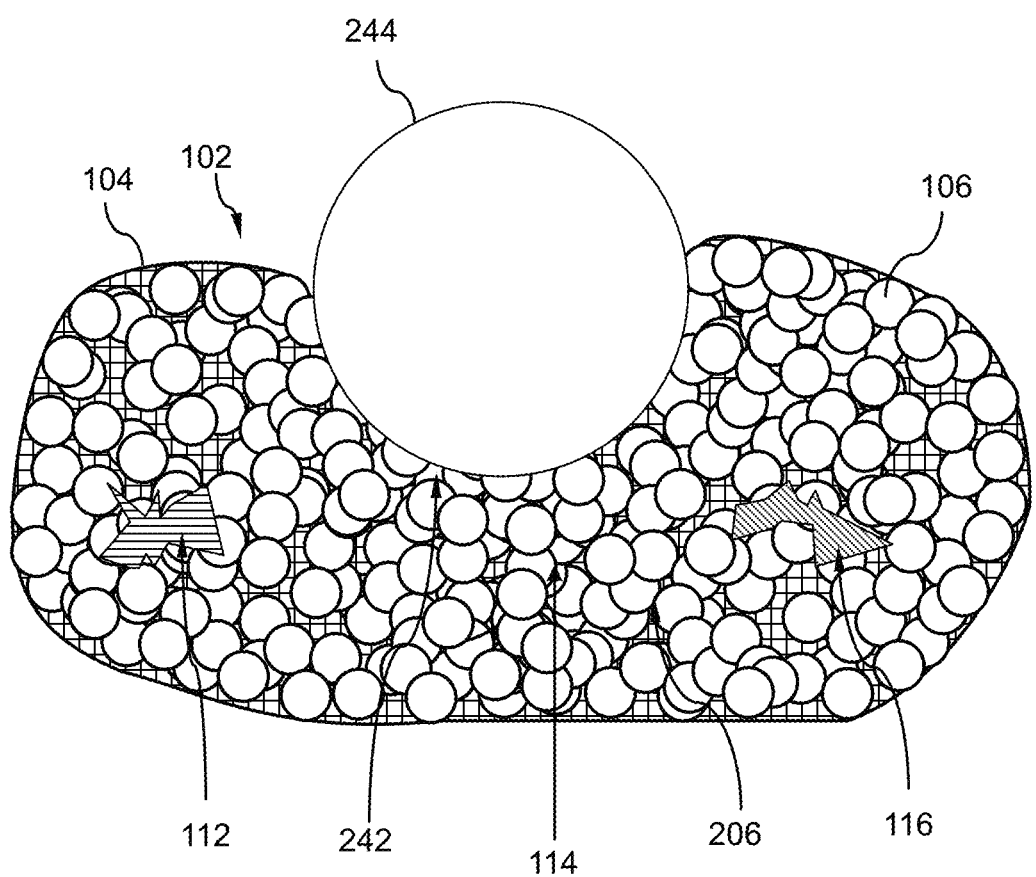
FIG. 3 is a schematic diagram illustrating a stabilizing cushion in a final configuration, according to one embodiment of the present invention.

FIG. 3 shows position-retaining device 102 in a final configuration 300 in which a polyurethane 312 formed by the reaction of isocyanate component 110 and polyol component 114 fills or substantially fills casing 104. In final configuration 300, position-retaining device 102 has been molded by hand around portion 242 of body part 244. Beads 106 embedded in polyurethane 312 provide a light, low density and moldable internal body that helps hold the shape of position-retaining device 102 during the molding of position-retaining device 102 while position-retaining device 102 is in intermediate configuration 200 and helps maintain the shape of position-retaining device 102 in final configuration 300. Polyurethane 312 surrounding beads 106 locks beads 106 in place, thereby further helping to maintain the shape of position-retaining device 102 in final configuration 300. In final configuration 300, position-retaining device 100 has a relatively stable shape that conforms to portion 242 of body part 244 and supports body part 244. Now empty rupturable container 112 and rupturable container 116 remain in position-retaining device 102 and become part of the hardened matrix.

In one embodiment, the rupturable containers may be thin and flimsy so that the empty rupturable containers do not significantly affect the shape of the position-retaining device.

The casing may be made of a woven fabric material of natural and/or synthetic fibers such cotton, silk, nylon, rayon, polyester, mixtures of fibers, etc. The casing may include a liner or may be made of multiple layers. In one embodiment, the casing may include a pull liner.

The rupturable container containing the isocyanate may be a made from a flexible material that is impervious to moisture such as aluminum, because the isocyanate component may react with water. In one embodiment of the present invention, the rupturable container containing the isocyanate may be rupturable sealed pouch made of aluminum foil with, for example, a very low moisture vapor transit rate.

The rupturable container containing the polyol may be a made from a variety of materials, such as plastics, that may or may not be impervious to moisture. In one embodiment of the present invention, the rupturable container containing the polyol component may be rupturable sealed pouch made of a plastic such a polyethylene, including high density polyethylene and low density polyethylene, polypropylene, polyvinylidene chloride, etc. In one embodiment, the rupturable container for the polyol may be made from a foil pouch or a foil-lined pouch that has a very low moisture vapor transit rate so that the rupturable container is a virtually moisture proof barrier.

The beads may be made of materials such as plastic, rubber, metal, wood, etc., that may be rigid or at least partially deformable. In one embodiment, the beads may be made of a non-puffed material. In one embodiment of the present invention, the beads may be made of relatively rigid plastic such as polystyrene, etc. The particular size and density of the beads used may vary depending on the particular application that the position-retaining device is used. The beads may have various shapes such as spherical, rod-shaped, cube-shaped, bar-shaped, cylindrically-shaped, star-shaped, toroidal, ovoid-shaped, V-shaped, L-shaped, I-beam-shaped, disk-shaped, pyramid-shaped, etc. In one embodiment of the present invention, the beads do not have sharp edges or corners to prevent the beads from damaging the rupturable containers and the casing and to ensure that the position-retaining device does not irritate the body part or portion of body part in contact with the position-retaining device. The beads may be solid or hollow. In some embodiments, the beads may made of a foamed material such as expanded polystyrene (EPS) or a closed-cell extruded polystyrene foam, e.g., Styrofoam®, to make the position-retaining device wider and/or to provide the position-retaining device with additional deformability and softness. In embodiments of the present invention where durability is important, a harder bead may be used.

In accordance to one embodiment of the present invention, the casing may include one or more oleophobic vents that allow gases, such as carbon dioxide ($CO_2$), to escape the casing but which do not allow any reagents or reagent mixtures to escape. The oleophobic vents facilitate removal of any gaseous by-product of the two-part polyurethane formation such as, for example, $CO_2$ that may be produced during the chemical reaction between the isocyanate component and the polyol component of the position-retaining device. Without the oleophobic vents, released gases may accumulate within the casing which may cause a balloon-type situation that allows too much movement of the patient and defeats the purpose of stabilization. The oleophobic vents will allow gasses (such as $CO_2$) to escape but not liquid such as, for example the chemical compositions or reagents used for binding and securing the internal moldable body of beads. In one embodiment, the oleophobic vents may have pores that are 0.5 to 5.0 µm in diameter.

An example of a position-retaining device, a stabilizing cushion, according to one embodiment of the present invention having oleophobic vents in the casing is shown in FIGS. 4, 5, 6, 7, 8 and 9.

Figure 4:
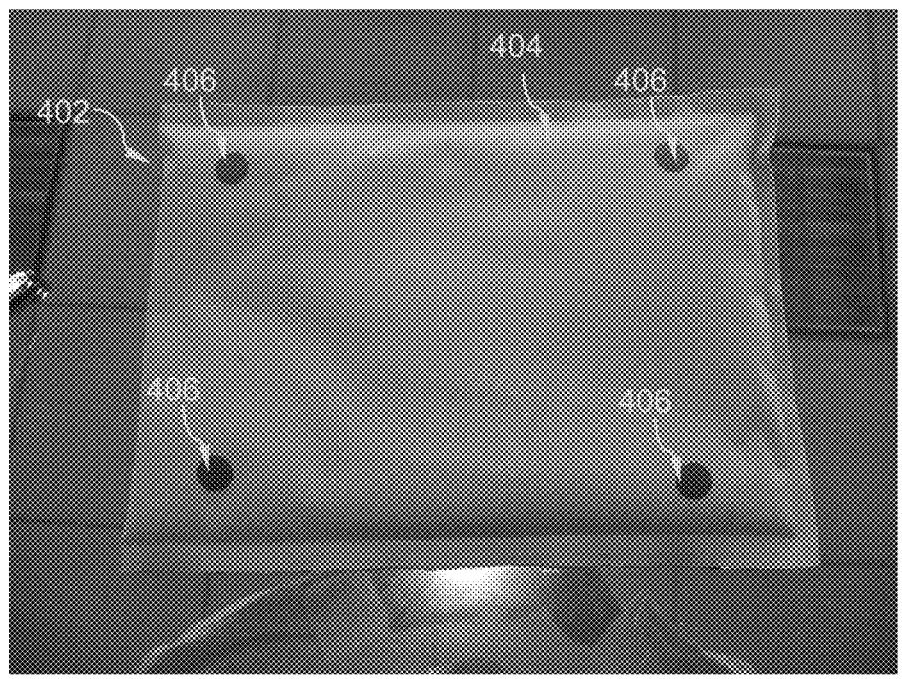
FIG. 4 is an image of the front of a stabilizing cushion in an initial configuration, according to one embodiment of the present invention.
Figure 5:
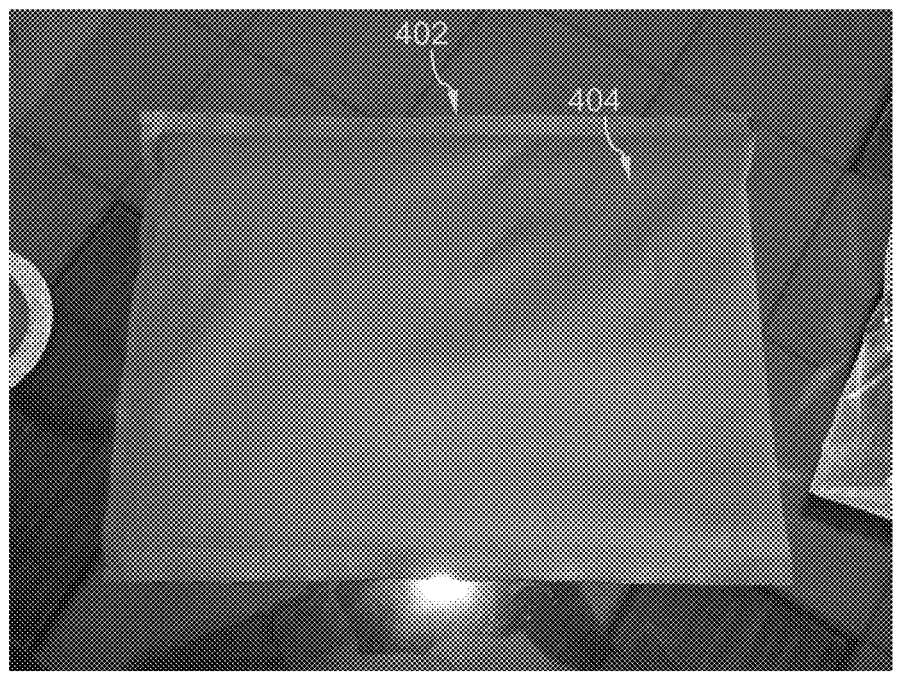
FIG. 5 is an image of the back of the stabilizing cushion of FIG. 4 in the initial configuration.
Figure 6:
FIG. 6 is an image of the stabilizing cushion of FIGS. 4 and 5 being molded into a shape in an intermediate configuration.
Figure 7:
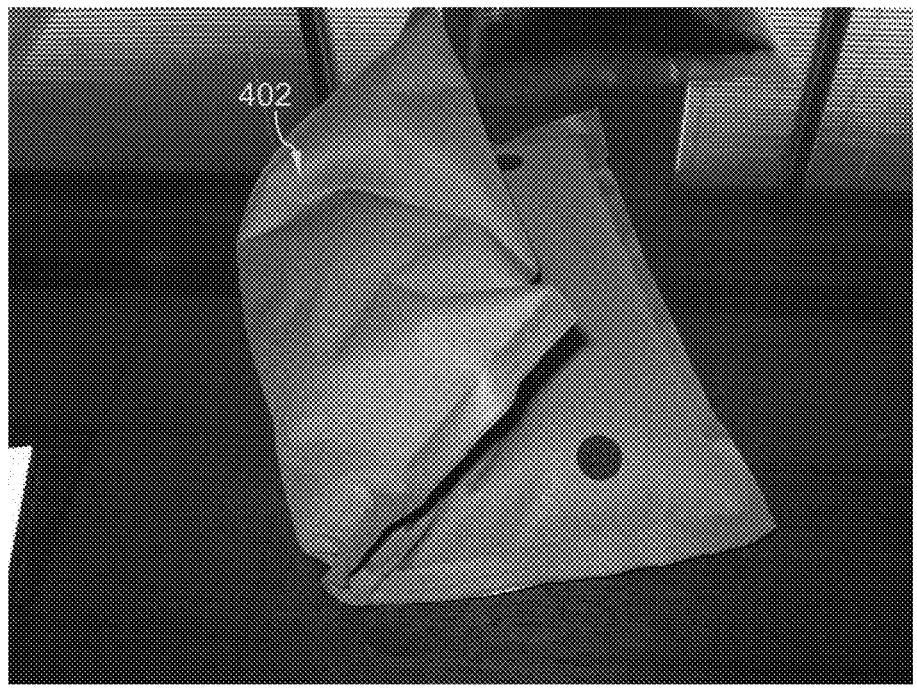
FIG. 7 is an image of the stabilizing cushion of FIG. 6 in the intermediate configuration.

FIG. 4 and FIG. 5 respectively illustrate a front and a back view of stabilizing cushion 402 in an initial configuration. Stabilizing cushion has a casing 404 having oleophobic vents 406. Casing 404 contains beads (not visible), a sealed aluminum pouch containing an isocyanate (not visible in FIGS. 4 and 5), and a sealed foil lined pouch containing a polyol (not visible). By squeezing on stabilizing cushion 402, the sealed pouch containing the isocyanate and the sealed pouch containing a polyol are ruptured, thereby allowing the isocyanate and polyol to react with each other to form a polyurethane that flows around beads. As the polyurethane is being form, stabilizing cushion 402 is molded into an intermediate configuration shown in FIG. 6 and FIG. 7.

Figure 8:
FIG. 8 is an image of the stabilizing cushion of FIGS. 6 and 7 in a final configuration.
Figure 9:
FIG. 9 is an image of the stabilizing cushion of FIG. 8 molded around the head of an individual.

FIG. 8 shows stabilizing cushion 402 in a final configuration in which the polyurethane has sufficiently filled casing 404 to lock the beads in place. FIG. 9 shows stabilizing cushion 402 molded around a portion 912, i.e., the back, of an individual's head 914. In one embodiment of the present invention, the stabilizing pillow may be utilized as an accessory to radiation therapy systems as a stand-alone device or in conjunction with a thermoplastic mask In accordance to one embodiment of the present invention, the casing may include one or more vent tubes that allow gases, such as carbon dioxide ($CO_2$), to escape the casing. To prevent reagents or reagent mixtures from escaping the casing, each vent tube may be plugged by a removable plug inserted in an open end of the vent tube. The removable plug may be removed after the reaction of reagent mixtures have started. One or more vent tubes may be used instead of oleophobic vents or in addition to oleophobic vents to allow gases to escape the casing. The vent tubes facilitate removal of any gaseous by-product of the two-part polyurethane formation such as, for example, $CO_2$ that may be produced during the chemical reaction between the isocyanate component and the polyol component of the position-retaining device. The one or more vent tubes prevent released gases that may accumulate within the casing from causing a balloon-type situation that allows too much movement of the patient and defeats the purpose of stabilization. The one or more vent tubes allow gasses (such as $CO_2$) to escape after the removable plug is removed from the vent tube. Prior to the removable plug being removed from a vent tube, liquids such as, for example the chemical compositions or reagents used for binding and securing the internal moldable body of beads are prevented from escaping from the casing by the removable plug.

In one embodiment of the present invention, instead of a removable plug, an open end of each vent tube may be covered by a removable cap to close or seal the vent tube in an initial configuration of the stabilizing cushion. In one embodiment of the present invention, each vent tube may be closed or sealed in an initial configuration of the stabilizing cushion and the one or more vent tubes may be opened by puncturing an end of each of the vent tubes, cutting off an end of each of the vent tubes, breaking of a sealed end of the vent tube from the rest of the vent tube at a weakened or frangible portion of the vent tube, etc.

Figure 10:
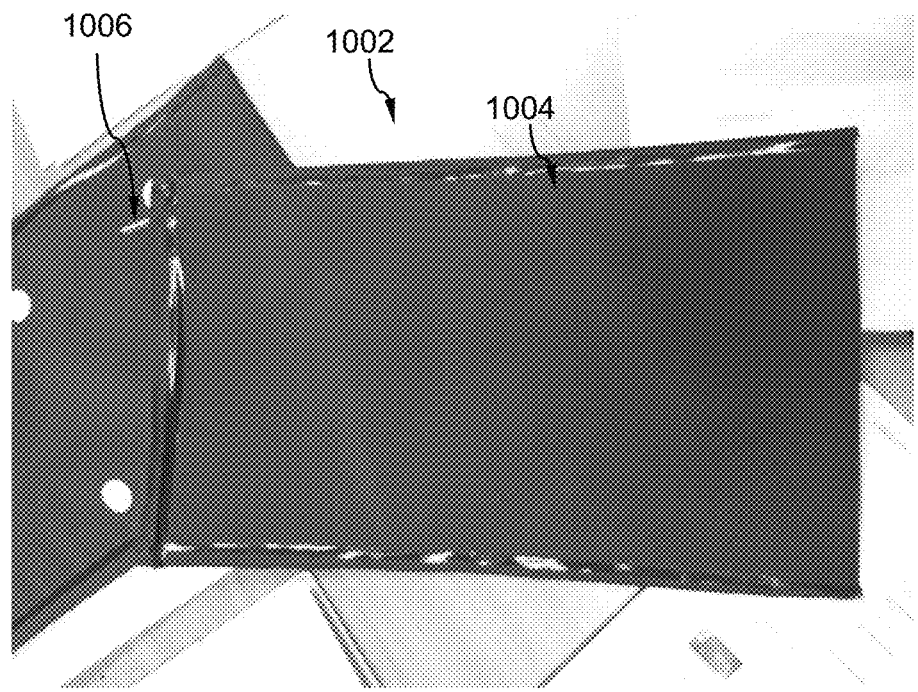
FIG. 10 is an image of the front of a stabilizing cushion including a vent tube in an initial configuration, according to one embodiment of the present invention.
Figure 11:
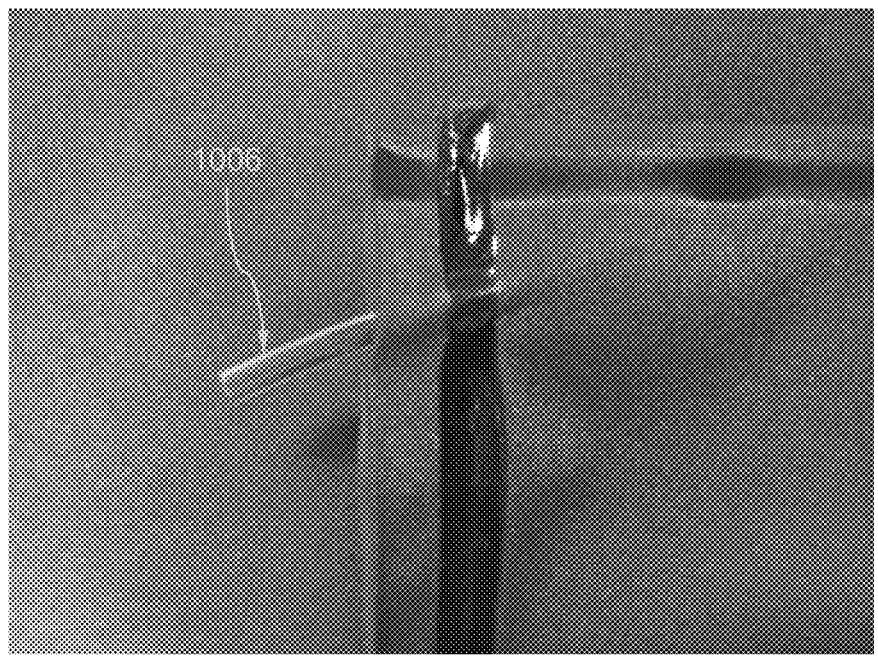
FIG. 11 is a close-up of the vent tube of FIG. 10.
Figure 12:
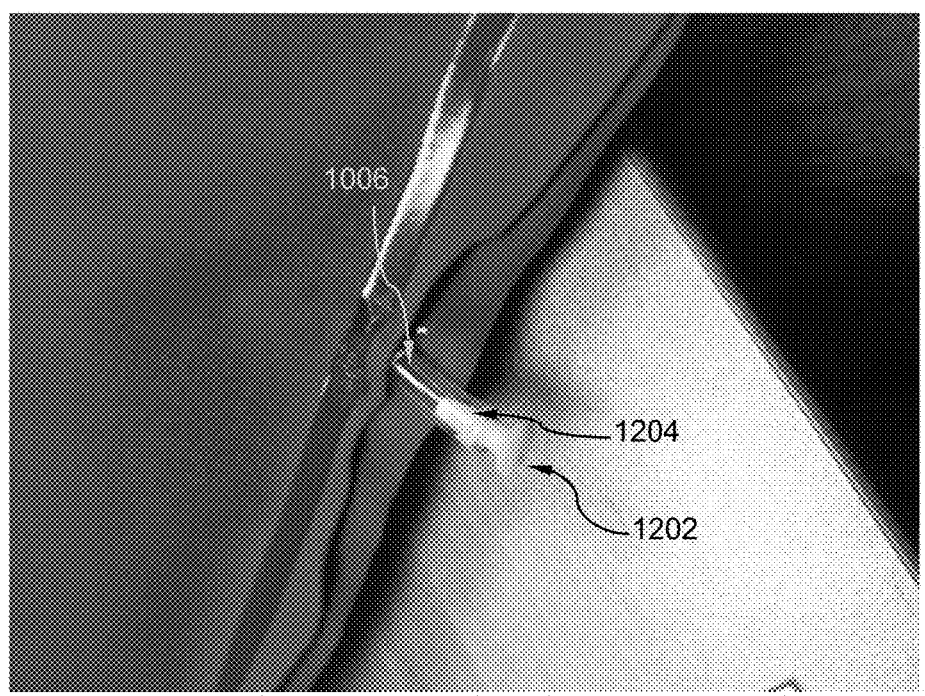
FIG. 12 shows the vent tube of FIG. 11 with a removable plug inserted in an open end of the vent tube to prevent liquid from escaping the casing through the vent tube.

An example of a position-retaining device, a stabilizing cushion, according to one embodiment of the present invention having a vent tube extending from the casing is shown in FIGS. 10, 11 and 12.

FIGS. 10, 11 and FIG. 12 respectively show a stabilizing cushion 1002 in an initial configuration. Stabilizing cushion 1002 has a casing 1004 having vent tube 1006. Casing 1004 contains beads (not visible), a sealed aluminum pouch containing an isocyanate (not visible in FIGS. 10, 11 and 12), and a sealed foil lined pouch containing a polyol (not visible). By squeezing on stabilizing cushion 1002, the sealed pouch containing the isocyanate and the sealed pouch containing a polyol are ruptured, thereby allowing the isocyanate and polyol to react with each other to form a polyurethane that flows around beads. FIG. 12 shows a removable plug 1202 inserted in an open end 1204 of vent tube 1006 to prevent liquids from escaping casing 1004 through vent tube 1006.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A device comprising a casing and having:
   an initial configuration, an intermediate configuration, and a final configuration,
   wherein in the initial configuration the casing contains: a plurality of beads, a rupturable first container containing one or more isocyanates and a rupturable second container containing one or more polyols,
   wherein in the final configuration the casing is substantially filled by a polyurethane in which the plurality of beads are embedded,
   wherein in the intermediate configuration the device is transformed from the initial configuration to the final configuration by rupturing the first container and rupturing the second container so that the one or more isocyanates react with the one or more polyols in a reaction that forms the polyurethane, and
   wherein as the polyurethane is formed during the reaction the polyurethane surrounds the plurality of beads.

2. The device of claim 1, wherein the device is in the initial configuration.

3. The device of claim 1, wherein the device is in the final configuration.

4. The device of claim 1, wherein the device is configured so that the device can be transformed from the initial configuration to the intermediate configuration by application of pressure upon the first container and the second container, respectively, through the casing.

5. The device of claim 1, wherein the casing comprises a fabric material.

6. The device of claim 5, wherein the fabric material includes one or more vents configured to allow gases formed by the reaction to escape the casing but prevent liquids from escaping the casing.

7. The device of claim 6 wherein the vents have pores that are 0.2 to 5.0 µm in diameter.

8. The device of claim 5, wherein the casing includes one or more vent tubes configured to allow gases formed by the reaction to escape the casing.

9. The device of claim 1, where wherein the first container is comprises of a material that is impervious to moisture.

10. The device of claim 9, wherein the first container comprises an aluminum pouch.

11. The device of claim 1, wherein the second container comprises a plastic pouch.

12. The device of claim 1, wherein the plurality of beads comprise polystyrene beads.

13. The device of claim 1, wherein the device comprises a stabilizing pillow.

14. A method comprising:
   transforming a position-retaining device from an initial configuration to an intermediate configuration, and
   transforming the position-retaining device from the intermediate configuration to a final configuration,
   wherein in the initial configuration, the position-retaining device comprises a casing containing: a plurality of beads, a rupturable first container containing one or more isocyanates and a rupturable second container containing one or more polyols,
   wherein transforming the position-retaining device from the initial configuration to an intermediate configuration comprises rupturing the first container and rupturing the second container through the casing so that the one or more isocyanates react with one or more polyols in a reaction that forms a polyurethane that surrounds a plurality of beads and substantially fills the casing,
   wherein transforming the position-retaining device from the intermediate configuration to the final configuration comprises molding the casing around at least a portion of a body part so that the position-retaining device conforms to the at least a portion of the body part while the polyurethane is being formed inside the casing, and wherein after the reaction is finished, the plurality of beads are embedded in the polyurethane so that the position-retaining device permanently conforms to the at least a portion of the body part.

15. The method of claim 14, wherein the first container and the second container are each ruptured by application of pressure upon the first container and the second container, respectively, through the casing.

16. The method of claim 14, wherein the casing comprises a fabric material.

17. The method of claim 16, wherein the fabric material includes one or more vents configured to allow gases formed by the reaction to escape the casing but prevent liquids from escaping the casing.

18. The method of claim 17 wherein the vents have pores that are 0.2 to 5.0 µm in diameter.

19. The method of claim 16, wherein the fabric material includes one or more vent tubes configured to allow gases formed by the reaction to escape the casing.

20. The method of claim 14, where wherein the first container is comprised of a material that is impervious to moisture.

21. The method of claim 20, wherein the first container comprises an aluminum pouch.

22. The method of claim 14, wherein the second container comprises a plastic pouch.

23. The method of claim 14, wherein the plurality of beads comprise polystyrene beads.

24. The method of claim 14, wherein the position-retaining device comprises a stabilizing pillow.

25. A product comprising the position-retaining device of claim 14 in the final configuration.

* * * * *